United States Patent [19]

Bres

[11] Patent Number: 4,868,269

[45] Date of Patent: Sep. 19, 1989

[54] PROCESS FOR THE PREPARATION OF N-SULPHONYL-N-(PHOSPHONOMETHYLGLYCYL) AMINES

[75] Inventor: Herve' Bres, Lyon, France

[73] Assignee: Rhone-Poulenc Agrochimie, Lyon, France

[21] Appl. No.: 937,720

[22] Filed: Dec. 4, 1986

[30] Foreign Application Priority Data

Dec. 4, 1985 [FR] France .................. 85 18148

[51] Int. Cl.$^4$ ................. C07F 9/38; C07F 9/40
[52] U.S. Cl. ....................... 558/145; 562/15
[58] Field of Search .................. 260/502.5 F, 502.5 P; 558/145

[56] References Cited

U.S. PATENT DOCUMENTS 4,233,056  11/1980  Maier .................. 260/502.5 F

FOREIGN PATENT DOCUMENTS 0135454  7/1984  European Pat. Off. .
2144425  3/1985  United Kingdom ............. 558/170

OTHER PUBLICATIONS

Kosolapoft et al., "Organic Phosphoraş Compounds", vol. 7, (1977), p. 10.
Houben-Weyl, "Methoden der Organischea Chemie", vol. X 11/1, (1967), p. 854.
Meomie, "Protective Groups in Organic Chemistry," (1973), pp. 62–63.

*Primary Examiner*—Anton H. Sutto
*Attorney, Agent, or Firm*—Morgan & Finnegan

[57] ABSTRACT

Preparation of compounds with herbicidal properties, of formula

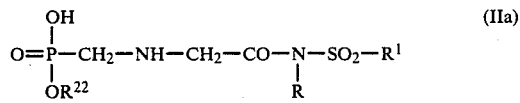

wherein
 $R^1$ represents a hydrocarbon radical;
 R represents a hydrogen atom or a hydrocarbon radical; and
 $R^{22}$ represents a hydrogen atom, an aryl radical, or a substituted aryl radical,
said process being characterized in that hydrogenation of compounds of formula

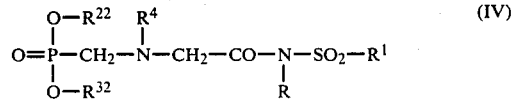

wherein R, $R^1$ and $R^{22}$ have the same meaning as in formula (IIa), $R^{32}$ represents an aryl radical, or substituted aryl radical, and $R^4$ represents a hydrogen atom or an $R^8$ group which can be hydrogenolyzed, is carried out.

20 Claims, No Drawings

PROCESS FOR THE PREPARATION OF N-SULPHONYL-N-(PHOSPHONOMETHYLGLYCYL) AMINES

BACKGROUND OF THE INVENTION

The present invention relates to a process for the preparation of N-sulphonyl-N-(phosphonomethylglycyl) amines which can be used as herbicides.

Products of the following formula are known (European Patent Application 135,454):

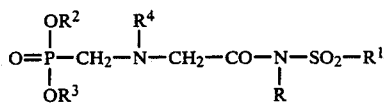

in which:

$R^1$ represents a hydrocarbon radical or substituted hydrocarbon radical especially an alkyl, aryl or cycloalkyl radical, the substituents preferably being halogen atoms or phenyl, cyano, alkyl, alkoxy or alkylcarboxylate groups, and the substituents more preferably being halogenated or selected from alkyl groups containing from 1 to 4 carbon atoms; and wherein $R^1$ preferably contains from 1 to 18 carbon atoms, more preferably from 1 to 7 carbon atoms, and (when $R^1$ is a cycloalkyl group) more preferably from 3 to 7 carbon atoms, and wherein $R^1$ is more preferably a chlorinated or fluorinated alkyl radical containing from 1 to 4 carbon atoms, e.g. $CF_3$;

R represents a hydrogen atom or has one of the meanings for $R^1$, and is preferably an alkyl group containing from 1 to 4 carbon atoms;

$R^2$ and $R^3$ each represent a hydrogen atom or are such that $OR^2$ and $OR^3$ are groups which can be hydrolyzed; $R^2$ and $R^3$ may preferably be an alkyl or aryl radical or substituted alkyl or aryl radical, and more preferably an alkyl radical or substituted alkyl radical; the substituents preferably being those mentioned for $R^1$, $R^2$ and $R^3$ generally containing from 1 to 12 carbon atoms and preferably containing from 1 to 8 carbon atoms; and $R^4$ represents a hydrogen atom or a group which can be hydrogenolyzed, represented by $R^8$, wherein $R^8$ is preferably a radical of formula $Ar(R^5)(R^6)C-$ in which Ar is an aromatic group, preferably phenyl, and $R^5$ and $R^6$ each are a hydrogen atom or an Ar radical or an alkyl group preferably containing not more than 6 carbon atoms;

and salts of these various products (especially salts of P-OH groups and those of nitrogen atom carrying $R^8$, which may be catagorized as an ammonium group), especially salts of these products which are acceptable in agriculture. Salts acceptable in agriculture include alkali metal salts, especially sodium and potassium salts, alkaline-earth metal salts, primary, secondary, tertiary or quaternary ammonium salts and sulphonium salts. Other salts of the invention are salts of addition with an acid such as chlorides, sulphates, phosphates and other salts derived from acids with a pK less than or equal to 2.5.

These products can be used as herbicides and/or as intermediates for the synthesis of herbicides.

It is also known to prepare products of the formula

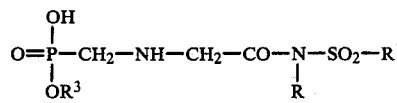

in which R, $R^1$ and $R^3$ have the same meaning as in formula (I), by a dual operation of hydrolysis and hydrogenolysis of a compound of formula (III):

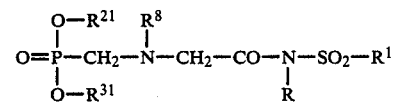

in which:

R, $R^1$ and $R^8$ have the same meaning as in formula (I), and $R^{21}$ and $R^{31}$ have the same meanings as $R^2$ and $R^3$, except that $R^{21}$ and $R^{31}$ do not represent the hydrogen atom.

The preparation of compounds of formula (II) from compounds of formula (III) is carried out by a hydrogenolysis involving the $R^8$ group and a hydrolysis involving the $R^{21}$ and/or $R^{31}$ groups.

One object of the invention is to provide a simplified process for the preparation of compounds of formula (I). Another object is to provide a process for the preparation of compounds of formula (I) which does not require hydrolysis.

Other objects and advantages of the invention will become apparent in the course of the description which follows.

SUMMARY OF THE INVENTION

It has now been found that these objects could be achieved by means of the process according to the invention. This invention is a process for the preparation of compounds and derivatives of compounds of formula (IIa)

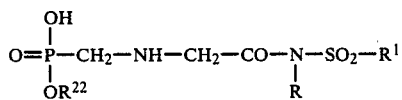

wherein R, $R^1$ have the same meaning as in formula (I) such that $R^1$ represents a hydrocarbon radical or substituted hydrocarbon radical, especially an alkyl, aryl or cycloalkyl radical, the substituents preferably being halogen atoms or phenyl, cyano, alkyl, alkoxy, or alkylcarboxylate groups, and the substituents more preferably being halogenated or selected from alkyl groups containing from 1 to 4 carbon atoms; and wherein $R^1$ preferably contains from 1 to 18 carbon atoms, more preferably from 1 to 7 carbon atoms, and (when $R^1$ is a cycloalkyl group) more preferably from 3 to 7 carbon atoms, and wherein $R^1$ is more preferably a chlorinated or fluorinated alkyl radical containing from 1 to 4 carbon atoms, e.g. $CF_3$;

R represents a hydrogen atom or has one of the meanings given for $R^1$, and is preferably an alkyl group containing from 1 to 4 carbon atoms; and $R^{22}$ represents a hydrogen atom, an aryl radical, or a substituted aryl radical, said process being characterized in that hydrogenation (also described as hydrogenolysis) of compounds of the formula IV $$\begin{array}{c} O-R^{22} \quad R^4 \\ | \quad\quad | \\ O=P-CH_2-N-CH_2-CO-N-SO_2-R^1 \\ | \quad\quad\quad\quad\quad\quad\quad | \\ O-R^{32} \quad\quad\quad\quad\quad R \end{array} \quad (IV)$$

wherein $R$, $R^1$ and $R^{22}$ have the same meaning as in formulas I and IIa;

$R^{32}$ represents an aryl radical, or substituted aryl radical; and $R^4$ represents a hydrogen atom or a group which can be hydrogenolyzed represented by $R^8$, wherein $R^8$ is preferably a radical of formula $Ar(R^5)(R^6)C-$ in which Ar is an aromatic group, preferably a phenyl group, and $R^5$ and $R^6$ are a hydrogen atom or an Ar radical or an alkyl group preferably containing not more than 6 carbon atoms, is carried out, said hydrogenation being carried out until the degree of conversion of the product of formula (IV) is greater than about 50% and preferably greater than about 85%. In the present account, the degree of conversion (or level of transformation) of the product of formula (IV) is considered relative to the radical $R^{32}$ and relative to the conversion of the $OR^{32}$ radical into an OH radical according to formula (IIa). Possible substituents for $R^{22}$ and $R^{32}$ include substituents for $R^1$ in formula (I).

According to the process of the invention, the product of formula (IV) is heated in the presence of a platinum-based catalyst. This platinum-based catalyst may be platinum metal or a platinum derivative, e.g. $PtO_2$, wherein the platinum derivative is a source of platinum metal under the reaction conditions.

A suitable catalyst for the process of the invention is one in which the metal is in a finely divided state. The catalyst can be deposited on a support. Supports which can be used are activated charcoal, silica, diatomaceous earth and other supports useful in hydrogenation reactions.

The quantity of catalyst employed is generally such that the ratio (by weight or by moles) of the catalyst metal relative to the product of formula (IV) is between 0.001 and 50, preferably between 0.01 and 10.

When a support is employed, the catalyst generally contains from about 0.01 to about 50% by weight of the metal relative to the support, preferably from about 1 to about 15%.

The reaction is advantageously carried out under a pressure of hydrogen ranging from about 1 to about 100 bars, preferably from about 5 to about 40 bars (absolute pressures).

The reaction temperature is generally between about 20 and about 150° C., preferably between about 50 and about 100° C.

The hydrogenation according to the invention may, if required, be accompanied by a salification.

The following non-limiting examples, illustrate the invention and its utility. The pressures indicated are absolute pressures (atmospheric pressure = 1 bar).

EXAMPLE 1

A 125-cc reactor is charged with:

N-benzyl-N-(diphenoxyphosphonomethyl)-N'-methyl-N"-methyl-N'-(methylsulphony)glycinamide (10 g; 0.02 mole) of formula:

$$\begin{array}{c} C_6H_5-O \\ | \\ O=P-CH_2-N-CH_2-CO-N-SO_2-CH_3 \\ | \quad\quad\quad\quad | \quad\quad\quad\quad | \\ C_6H_5-O \quad CH_2-C_6H_5 \quad CH_3 \end{array} \quad (V)$$

$PtO_2$ (Adam's platinum) (0.2 g)
$CH_3COOH$ (50 cc).

The contents are heated for 5 h 30 min at 60° C. under 21 bars of hydrogen.

The catalyst is filtered washed and recycled.

By chromatography, it is observed that a product (3.48 g; 13.38 millimoles) of the following formula is obtained:

$$\begin{array}{c} OH \\ | \\ O=P-CH_2-NH-CH_2-CO-N-SO_2-CH_3 \\ | \quad\quad\quad\quad\quad\quad\quad\quad | \\ OH \quad\quad\quad\quad\quad\quad\quad\quad CH_3 \end{array} \quad (VI)$$

The product yield is 67%, and the degree of conversion of the starting product is 100%.

An advantage of the process according to the invention is that compounds such as those of formula (V) may be obtained with a high degree of purity (and are therefore especially suited for crystallization).

EXAMPLE 2

A 125-cc stainless steel autoclave is charged with the product (2 g; 5.95 millimoles) of formula (VII):

$$\begin{array}{c} O-C_6H_5 \\ | \\ O=P-CH_2-NH-CH_2-CO-N-SO_2-CH_3 \\ | \quad\quad\quad\quad\quad\quad\quad\quad | \\ OH \quad\quad\quad\quad\quad\quad\quad\quad CH_3 \end{array} \quad (VII)$$

and $PtO_2$ (10 mg) in water (50 cc). The autoclave is pressurized to 21 bars and heated for 4 hours at 80° C.

The catalyst is filtered and recovered.

By chromatography of the liquid phase of the reaction mixture, it is observed that a product (0.54 g; 2.08 millimoles) of formula (VI), amounting to a yield of 35%, is obtained. The degree of conversion of the starting product is 63%.

EXAMPLE 3

A similar reactor is charged with the product (2 g) of formula (VII) and a mixture of $CH_3COOH$ (20 cc) and a catalyst (0.297 g) containing 5% of finely divided platinum deposited on an activated charcoal support.

The contents are heated for 5 h at 80° C. under an atmosphere of 21 bars of hydrogen (absolute pressure).

The catalyst if filtered, washed and recycled.

By chromatography, it is observed that a product (1.02 g) of formula (VI), amounting to a yield of 66%, is obtained. The degree of conversion of the starting product is 95%.

EXAMPLE 4

Example 3 is repeated, but using 0.148 g of the catalyst instead of 0.297 g and heating for 5 h 30 min instead of 5 h.

A product (1.036 g) of formula (VI), amounting to a yield of 67% is obtained. The degree of conversion of the starting product is 76%.

EXAMPLE 5

Example 1 is repeated, but using 2 g of the catalyst containing 5% of platinum deposited on activated charcoal and heating at 65° C. instead of 60° C.

A product of formula (VI) is obtained, with a yield of 45%. The degree of conversion of the starting product is 100%.

What is claimed is:

1. A process for producing compounds and salts of compounds of formula IIa

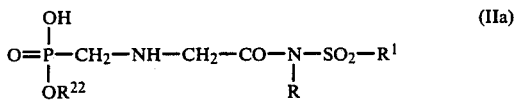

wherein $R^1$ represents an alkyl, aryl or cycloalkyl radical or substituted alkyl, aryl or cycloalkyl radical;

R represents a hydrogen atom or an alkyl, aryl or cycloalkyl radical or a substituted alkyl, aryl or cycloalkyl radical; and $R^{22}$ represents a hydrogen atom or an aryl radical or a substituted aryl radical, said process comprising hydrogenation of compounds of formula IV

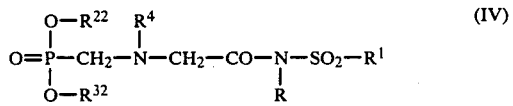

wherein $R^1$ represents an alkyl, aryl or cycloalkyl radical or a substituted alkyl, aryl or cycloalkyl radical;

R represents a hydrogen atom or an alkyl, aryl or cycloalkyl radical or a substituted alkyl, aryl or cycloalkyl radical; and $R^4$ represents a hydrogen atom or an $R^8$ group which can be hydrogenolyzed, wherein the $R^8$ group is a radical according to the formula $Ar(R^5)(R^6)C-$, in which Ar is an aromatic group and both $R^5$ and $R^6$ are selected from the group consisting of a hydrogen atom, an aromatic radical, and an alkyl group;

$R^{22}$ represents a hydrogen atom or an aryl radical or a substituted aryl radical; and $R^{32}$ represents an aryl radical or a substituted aryl radical, said hydrogenation being carried out under elevated temperature and in the presence of a platinum-based catalyst until conversion of the compound of formula IV is greater than about 50%.

2. A process according to claim 1, wherein $R^1$ and R, same or different, contain from 1 to 18 carbon atoms.

3. A process according to claim 1, wherein $R^1$ and R, same or different, contain 1 to 7 carbon atoms.

4. A process according to claim 1, wherein $R^1$ and R, same or different, are cycloalkyl groups containing from 3 to 7 carbon atoms.

5. A process according to claim 1, wherein R and $R^1$ are methyl radicals, $R^4$ is hydrogen or a benzyl radical, $R^{22}$ is hydrogen or a phenyl radical, and $R^{32}$ is a phenyl radical.

6. A process according to claim 1, wherein the reaction is carried out under a hydrogen pressure between about 1 and 100 bars.

7. A process according to claim 1, wherein the reaction is carried out at a temperature between about 20° and about 150° C.

8. A process according to claim 1, wherein conversion of the compound of formula IV is greater than about 85%.

9. A process according to claim 1, wherein the aromatic group is a phenyl group.

10. A process according to claim 1, wherein $R^5$ and $R^6$, same or different, are alkyl groups containing not more than 6 carbon atoms.

11. A process according to claim 1, wherein the nitrogen atom bonded to $R^8$ is a substituted ammonium group.

12. A process according to claim 1, wherein the substituents are selected from the group consisting of halogen atoms, phenyl groups, cyano groups, alkyl groups, alkoxy groups, and alkylcarboxylate groups.

13. A process according to claim 12, wherein the substituents are halogenated.

14. A process according to claim 12, wherein the substituents are selected from alkyl groups containing from 1 to 4 carbon atoms.

15. A process according to claim 12, wherein $R^1$ and R, same or different, are chlorinated or fluorinated alkyl radicals containing from 1 to 4 carbon atoms.

16. A process according to claim 15, wherein the substituent is $CF_3$.

17. A process according to claim 1, wherein the amount of catalyst employed is generally such that the mole or weight of the catalyst to the compound of formula IV is between about 0.001 and about 50.

18. A process according to claim 1, wherein the catalyst is in a finely divided state.

19. A process according to claim 18, wherein the catalyst is deposited on a support such as activated charcoal, silica, or diatomaceous earth.

20. A process according to claim 19, wherein the amount of weight of metal contained in the catalyst relative to the weight of the support is between about 0.01% and about 50%.

* * * * *